(12) United States Patent
Michels

(10) Patent No.: US 6,332,877 B1
(45) Date of Patent: *Dec. 25, 2001

(54) OSTOMY TUBE PLACEMENT TIP

(75) Inventor: Lester D. Michels, Eden Prairie, MN (US)

(73) Assignee: Novartis AG, Berne (CH)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/076,442

(22) Filed: May 12, 1998

(51) Int. Cl.[7] ............... A61M 5/00; A61M 31/00
(52) U.S. Cl. ............ 604/263; 604/270; 604/275; 604/910
(58) Field of Search ............... 604/263, 264, 604/256, 265, 270, 275, 523, 910, 93, 192, 288

(56) References Cited

U.S. PATENT DOCUMENTS

| 2,603,217 | * | 7/1952 | McShirley | 128/239 |
|---|---|---|---|---|
| 3,640,281 | * | 2/1972 | Robertson | 128/347 |
| 4,143,651 | * | 3/1979 | Patel | 128/349 B |
| 4,361,152 | * | 11/1982 | Patel | 604/99 |
| 4,393,873 | * | 7/1983 | Nawash et al. | 604/151 |
| 4,516,970 | | 5/1985 | Kaufman et al. | 604/270 |
| 4,698,056 | * | 10/1987 | Ciannella | 604/164 |
| 4,936,835 | * | 6/1990 | Haaga | 604/265 |
| 4,944,732 | | 7/1990 | Russo | 604/247 |
| 5,049,138 | * | 9/1991 | Chevalier | 604/265 |
| 5,407,437 | * | 4/1995 | Heimreid | 604/256 |
| 5,413,565 | | 5/1995 | Michels et al. | 604/247 |
| 5,454,790 | | 10/1995 | Dubrul | 604/104 |
| 5,474,542 | * | 12/1995 | Gandi et al. | 604/265 |
| 5,522,801 | | 6/1996 | Wang | 604/96 |
| 5,722,933 | * | 3/1998 | Yabe et al. | 600/123 |
| 5,860,916 | * | 1/1999 | Pylant | 600/208 |
| 6,077,275 | * | 6/2000 | Bryars | 606/139 |

FOREIGN PATENT DOCUMENTS

| 0 437 248 | 7/1991 | (EP) . |
|---|---|---|
| 2 103 936 | 3/1983 | (GB) . |
| 91/07200 | 5/1991 | (WO) . |
| 94/25093 | 11/1994 | (WO) . |

* cited by examiner

Primary Examiner—Richard K. Seidel
Assistant Examiner—Michael J. Hayes
(74) Attorney, Agent, or Firm—Hesna J. Pfeiffer; Michael U. Lee

(57) ABSTRACT

A catheter or ostomy tube placement tip is comprised of a tapered, substantially conical head portion and a cylindrical body or stem portion centrally attached to the base thereof. The cylindrical base fits snugly within the lumen of a catheter or ostomy tube such as a ostomy or jejunal feeding tube and its tapered design allows for the insertion and placement of the tube within the lumen of the stomach or other body cavity through an opening or ostomy. Once properly placed, the tip is discharged from the end of the tube so that it is dissolved by human body fluids and is excreted.

5 Claims, 4 Drawing Sheets

OSTOMY TUBE PLACEMENT TIP

FIELD OF THE INVENTION

The present invention relates generally to catheters and medical devices comprising ostomy tubes for the insertion into a mammalian body, preferably humans. In particular, the invention relates to feeding tubes and their placement and securement to a patient.

BACKGROUND OF THE INVENTION

The use of enteral feeding tubes which supply nutritional requirements of a patient directly to the stomach or other location in the digestive tract is often required when the patient for one reason or another cannot swallow, is unable to chew his or her food, or is unable to ingest enough food to meet the body's caloric requirements. Burn victims, the chronically ill, those inflicted with Alzheimer's disease and cancer patients are prime examples of these types of individuals. Enteral feeding usually employs a nasogastric tube to transport the liquid nutritional products through the nasal cavity and pharayrx and into the stomach.

Gastrostomy tubes may either be placed through the surgical creation of an ostomy while the patient is under general anesthesia or by means of percutaneous endoscopic gastrostomy (PEG) which involves the creation of an opening or stoma in the stomach through the abdominal wall. The endoscope is passed down the throat until its terminus contacts the interior of the stomach. A needle with a stylet is inserted into the stomach wall until it passes therethrough. The stylet of the needle is retracted and a guidewire inserted through the cannula of the needle. The guidewire is grasped and pulled back through the esophagus and out of the mouth with the endoscope. The gastrostomy tube is attached to the guidewire at the mouth while the opposite end of the guidewire protrudes from the cannula needle. Pulling the guidewire at the cannula directs the gastrostomy tube down the esophagus and into the stomach and eventually into the tract created by the cannula needle.

U.S. Pat. No. 4,516,970 to Kaufman et al. discloses a catheter or feeding tube in which the front end portion that enters the patient's body is comprised of a weighted bolus tip. The weighted tip may either be open-ended in which the tip comprises a central lumen which is confluent with the lumen of the feeding tube or may be of solid construction in which the feeding tube adjacent thereto is perforated for delivery of the nutritional/medicinal fluids to the patient. The tip is intended to facilitate insertion of the feeding tube into the stoma of a patient.

U.S. Pat. No. 4,944,732 to Russo discloses a gastrostomy feeding port comprising a definable, conical tip portion with at least one opening therein for the discharge of nutritional or medicinal liquids, a tube portion that is confluent with the opening in the tip and extends rearwardly therefrom and a fitting with a removable flange and valve at the rear end of the tube portion. In use, the tip is inserted into the stomach through a surgically incised stoma in the skin of the patient. The flange and fitting portion secure the tube to the skin of the patient at the stoma. The tip portion is designed so that upon pressing it against the stoma, the tip is deformed to an elongated configuration so that it can be more easily passed through the stoma. Lubricants and associated anesthetics can be applied to the surface of the tip for even easier insertion.

U.S. Pat. No. 5,413,565 to Michels et al. teaches and claims a gastrostomy feeding port comprising an elastic, conically-shaped tip adaptable to fit a variety of different stoma lengths. The conical tip is attached to a middle tube portion and a retaining flange. The tip has an opening which is confluent with the central lumen of the feeding tube and through which nutritional and/or medicinal fluids are fed to the patient. The tip portion is collapsible, a feature which facilitates entry of the feeding tube into the stomach through the ostomy and its subsequent removal thereof. The tip is also provided with anchoring means to secure the tube to the inside of the stomach. The flange portion, is positioned some distance down the tube from the tip and secures the tip externally to the skin of the patient.

U.S. Pat. No. 5,454,790 to Dubrul discloses a catheter and method for its use in the percutaneous placement of feeding and drainage tubes comprising an elastic access tube in an internal stylet. The stylet has a sharpened distal tip which extends beyond the distal end of the access tube. The tip may be inserted through previously incised ostomy or may directly penetrate the skin and stoma of the patient. The access tube is then guided over the tip and the internal tube until it also penetrates the stomach. The gastrostomy feeding tube is then guided thereover.

Finally, U.S. Pat. No. 5,522,801 to Wang teaches and claims an integrated silicone balloon catheter comprising a shaft which defines a drainage lumen with a longitudinal groove on the outside, a conical tip attached to one end of the shaft and a sheath bonded to and disposed around the shaft. The sheath is inflatable and the tip is used to guide the catheter primarily through naturally occurring lumens in the body such as the urethra, anus, esophagus and the like.

All of the devices disclosed in the prior art are relatively complex structures which are manufactured as an integral part of the gastrostomy feeding tube or catheter itself. Not all facilitate easy and direct insertion of the catheter or ostomy tube itself, for example the blunt end tips, and moreover, none of these devices allow for the very simple removal thereof since the bulbous head or tip must somehow be withdrawn either endoscopically up and out through the gastrointestinal tract or it must be pulled back out through the ostomy, thereby possible resulting in further abrasion and discomfort to the patient. In addition, insertion of the tapered tips of the prior art exposes the gut wall opposite to the insertion point to damage if the tip is inadvertently forced or pressed against it.

It is an object of the present invention to provide a one-piece tapered and/or rounded tip for use in the insertion of catheters and ostomy tubes such as gastrostomy feeding tubes for the delivery of nutritional and medicinal fluids to patients. It is a further object of the present invention to provide a conically-shaped tip that is detachably inserted into the end of the gastrostomy feeding tube for simple placement, guidance and insertion of the tube through a pre-incised ostomy in the skin and fascia of a patient.

It is a further object of the present invention to provide a conical tip that is simple to manufacture in a large number of sizes and designs so as to be readily attached to a wide variety of feeding tubes at the time of placement. Finally, it is an object of the invention to provide a conical, flexible tip that can be detachably inserted into the distal end of a catheter or gastrostomy feeding tube so that once the tube is properly placed in the stomach or small intestine, the tip can be readily detached from the tube into the body of the patient where it is readily dissolved and/or discharged therefrom.

SUMMARY OF THE INVENTION

Figure 1:
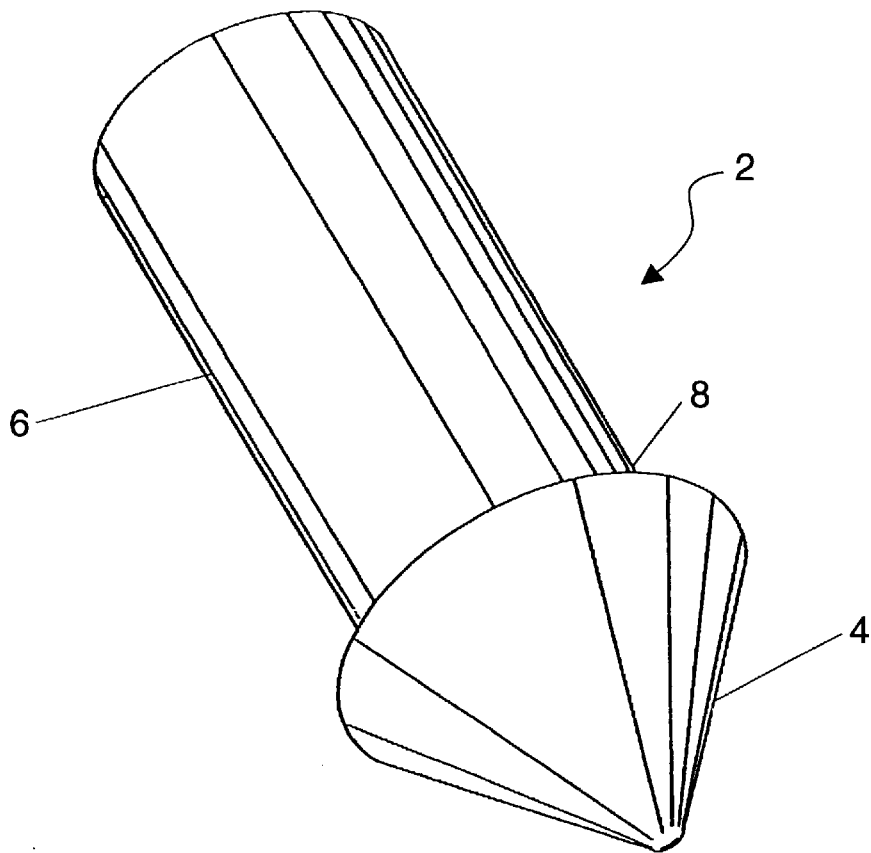
FIG. 1 is an overall schematic view of the conical insertion tip in the plug design embodiment of the present invention.

The ostomy tube placement tip of the present invention is a simple design that is comprised of a tapered, substantially conical head portion and a body or stem portion. The body is located at the base of the conical head and is perpendicular to the plane formed thereby. The body or stem is inserted into the conduits formed by the inner walls of a catheter, ostomy tube or, preferably, a gastrostomy or jejunal feeding tube and is snugly maintained therein. In this way, at least in one embodiment, it also serves to plug the end of the tube. The tapered design of the conical head allows for an easy insertion of the tube into a pre-incised ostomy with little friction or abrasion of the skin, fascia, peritoneum and other tissues. Once the tube is placed, the tip can be detached into the stomach or other body cavity where it is readily dissolved and/or excreted by the digestive system.

DETAILED DESCRIPTION OF THE INVENTION

Whereas the ostomy replacement tip of the present invention can be used in conjunction with a variety of ostomy tubes, catheters, drainage tubes and the like, it is particularly useful as a guidance tip for gastrostomy and jejunal feeding tubes. The ostomy tube placement tip of the present invention is comprised of a substantially conical tip portion and a body portion extending from the base of the core. The body portion has a circumference that closely approximates that of the inner walls of the catheter or ostomy tube that forms the conduit for the liquid medicinal or nutritional formula.

In the alternative, if the ostomy tube, drainage tube or catheter comprises more than one lumen, the body or plug portion may be designed to comprise one or more extensions for insertion into each of the multiple lumens.

When in use, the body portion, which is preferably cylindrical, is inserted into the conduits of the tube and since the circumference of both the conduits and the body portions are substantially the same size, the insertion results in a fairly snug fit so that if jostled, the placement tip will not readily detach without some exertion of force. Preferably, the base of the conical portion rests flush against the end of the ostomy tube upon insertion.

The simplistic design of the ostomy tube placement tips of the present invention makes them easy to manufacture and hence relatively inexpensive in cost. Due to the need for a snug fit between the body portion and the inner wall of the ostomy tube, the size of the placement tip may vary according to what size tube the tip will be used with. The circumference of the body portion where it joins the base of the tapered tip will substantially equal that of the inner wall of the ostomy tube that forms the conduit for the delivery of nutritional and/or medicinal formula. The circumference of the base of the conical tip may be less or greater than the circumference of the ostomy tube, but preferably will essentially equal that of the outer external circumference of the tube. Most preferably, when properly inserted, the outer surfaces of both the conical base and tube will be uniformly aligned.

The conical shaped head portion allows for the easy insertion of the ostomy tube into a previously incised ostomy of the patient to be administered formula or medicine directly to the stomach. Similar to an "arrow" or "spear" shape, the tip first contacts the patient and enters the ostomy at its distal point, the place of the smallest size of the diameter of the tip. As the tip is pushed into the ostomy and further through the peritoneum and outer wall of the stomach, the circumference of the tip gradually expands the size of the folds of the peripheral ostomy. In this manner, the tip gradually expands the size of the ostomy with little friction, abrasion or tearing until the ostomy can accommodate the circumference of the entire tube itself.

Referring now to FIG. 1, a preferred embodiment of the ostomy tube placement tip (2) is shown by itself, disassociated from the ostomy tube within which it is placed when in use. The tip is comprised of the tapered head portion (4) and the body portion (6) attached or joined at the base (8) thereof. As is evident from FIG. 1, the placement tip can be readily molded using methods and mold devices well known in the art. For example, the tip may be of unitary design and construction. Preferably, the tip is molded out of water soluble polymers, such as those typically used in absorbable sutures (Vicryl®), or non-toxic compounds that readily dissolve, whether by hydrolysis, digestion or other means within the stomach or other parts of the digestive tract. Suitable compounds include for example, polylactide polymers and copolymers, cellulose and cellulose derivatives such as carboxyl methyl cellulose, hydroxycellulose, hydroxymethyl cellulose, pectin, gums and derivatized gums such as guar, xanthan and acacia gums, starch, amylose, amylopectin and mixtures thereof.

Figure 2:
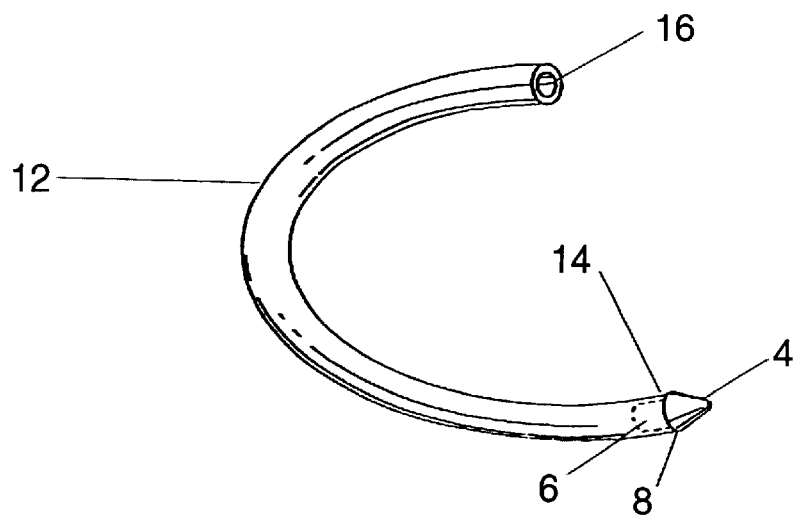
FIG. 2 is a side cut-away view of the conical tip in association with the gastrostomy feeding tube.
Figure 3:
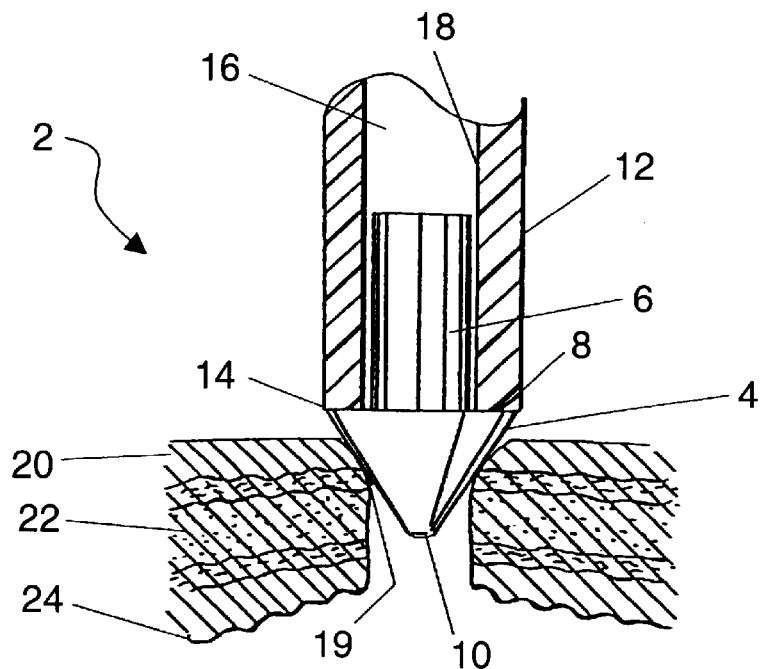
FIG. 3 is a side cut-away view of the tip and gastrostomy tube entering a patient's body through an ostomy.

Referring now to FIGS. 2 and 3, the ostomy tube placement tip (2) is shown inserted within and in association with a gastrostomy or jejunal feeding tube (12) that it guides into the ostomy incised in the abdomen, stomach or other body cavity. The base (8) of the placement tip (4) is inserted into the distal end (14) of the ostomy tube (12). The body portions (6) are pushed snugly within the conduit (16) formed by the inner wall (18) of the tube. Since the circumference of the body (6) closely approximates that of the conduit (16), the fit that results from pressing the tip (2) into the tube (12) is snug, but not overly tight to make detachment therefrom difficult or impossible.

Referring now more specifically to FIG. 3, the ostomy tube placement tip (2) together with the ostomy tube (12) is shown entering an ostomy (19) incised into the abdomen of a patient. The tip (10) of the conical head (4) gently spreads the peripheral folds of the ostomy (19) as the placement tip (2) and tube (12) is pressed inward against the skin (20), peritoneum (22), and stomach wall (24). The tapered design of the conical head (4) gradually expands the size of the ostomy's orifice until it is substantially the same size as the circumference of the head's base (8). At this juncture, the size of the opening of the ostomy is substantially the same as that of the outer circumference of the ostomy tube (12) which readily enters the ostomy and stomach wall.

Figure 4:
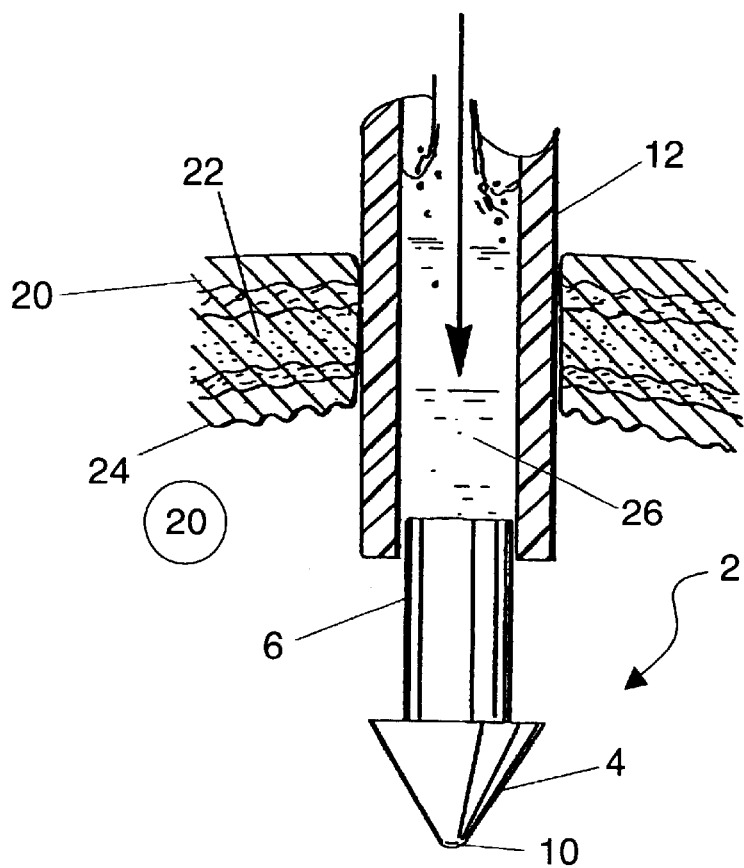
FIG. 4 is an overall schematic view of the conical tip being subsequently detached from the tube and discharged into the stomach of the patient.

Once the tube is placed within the stomach or other body cavity of the patient, the placement tip can be readily detached therefrom so that the ostomy tube conduit is open for the delivery of nutritional or medicinal formula. FIG. 4 shows the tips' (2) expulsion from the conduit of the tube into the patients' stomach (20). The force necessary for such expulsion can be supplied by pressurized gas or air, pressurized liquids such as water (26) and/or the use of a stylet pushed and fed through the lumen of the tube. Once the tip is detached, it is readily dissolved by the body fluids of the patient or is expelled by way of the digestive tract. The lumen of the feeding tube being opened, nutritional or medicinal formula can be administered to the patient.

Figure 5:
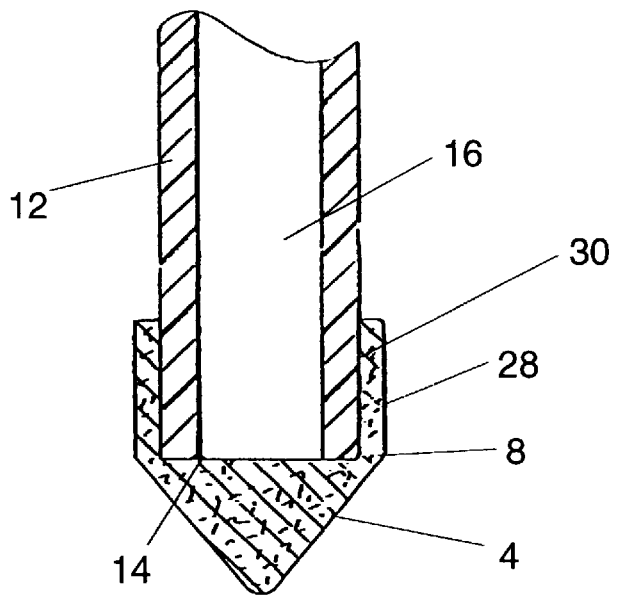
FIG. 5 is a cross-sectional side view of an alternative embodiment of the ostomy placement tip of the present invention in which the tip is formed like a cap that fits over the end of the tube and about its circumference.

Referring now to FIG. 5, a second embodiment of the ostomy tube placement tip of the present invention is shown in a cross-sectional side view together with the end of an associated ostomy tube (12). As opposed to the embodiment disclosed in FIGS. 1–4 wherein the narrower body portion (6) is inserted into the lumen of the ostomy tube and engages the inner walls thereof (18), i.e., like a "plug", here the outer periphery of the tapered head (4) extends as a cylindrical skirt (28) for some distance posteriorly from the circumference or periphery base of the cap (8). In this manner, the ostomy placement tip is inserted over the end of the tube (14) about its periphery (30). Rather than "plugging" the lumen with the body to maintain frictional adhesion with the tube, this cap design snugly fits about the tubes periphery and the base of the tapered head (8) covers the opening of the lumen (16) accordingly. As with the embodiment disclosed in FIGS. 1–4, once the tube is properly inserted and placed within the body cavity of the patient, the "cap design" tip detached by expulsion using a pressurized fluid or gas or by the insertion of a stylet (see FIG. 4). Once discharged, the cap is either digested or readily excreted in the feces.

Figure 6:
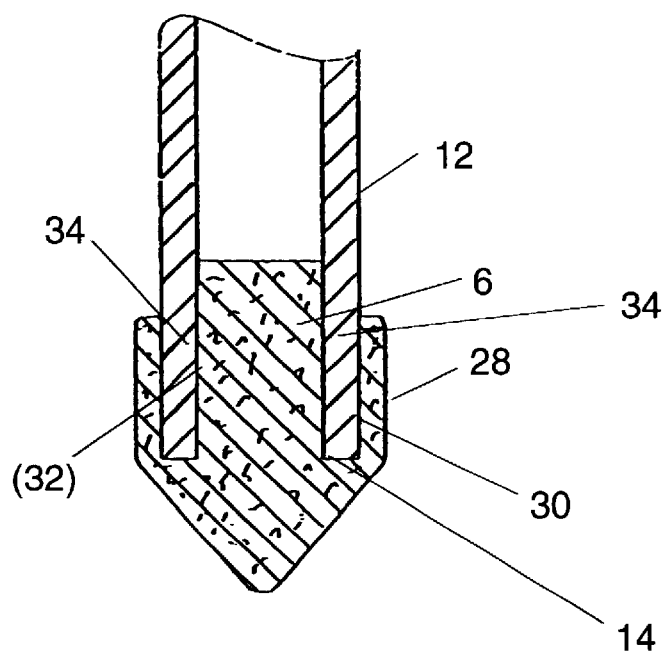
FIG. 6 is a cross-sectional side view of yet another alternative embodiment of the ostomy placement tip of the present invention in which the design comprises a hybrid of the cap and plug designs.

Referring now to FIG. 6, this cross-sectional side view is somewhat of a hybrid design combining the features of the tips disclosed in FIGS. 1 and 5, supra. The tip is shown as applied and finctionally associated with a respective ostomy tube. This design utilizes both the cylindrical body portion (6) for engaging the inner walls of the ostomy tube (18) when inserted therein but also comprises the outer cylindrical skirt (28) that slides over the periphery of the tube.

The inner wall of the skirt (30) and the peripheral surface of the cylindrical body (32) forms a circular well (34) for receiving the end of the tip (14) and the circular well (34) formed by the gap disposed between the inner wall of the cylindrical skirt (30) and the outer periphery of the cylindrical body (16) is such that the fit is snug, but not tight. This allows for easy detachment of the tip from the tube into the respective body cavity once the tube is properly in place for digestion or excretion. The physical dimensions of the body (16) and skirt (28) may vary in both thickness and length and may be tailored to properly fit the particular ostomy tube involved. The diameter of the cylindrical body may vary in size as does the diameter of the lumens of any standard ostomy tube or catheter. The thickness of the skirt (28) is dictated by the diameter of the tube and will only be that which is sufficient to provide a sturdy, snug fit while not making the overall circumference of the base of the tip head much greater than that of the circumference tube itself.

Figure 7:
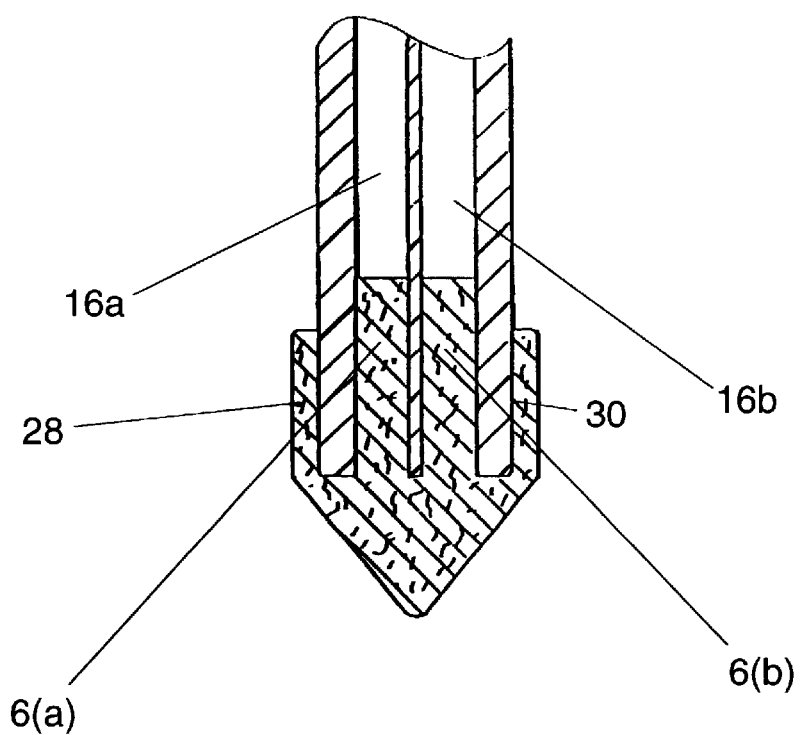
FIG. 7 is a cross-sectional side view of the ostomy placement tip of the present invention for multiple lumen (in this case 2) ostomy tubes utilizing a cap and plug design.
Figure 8:
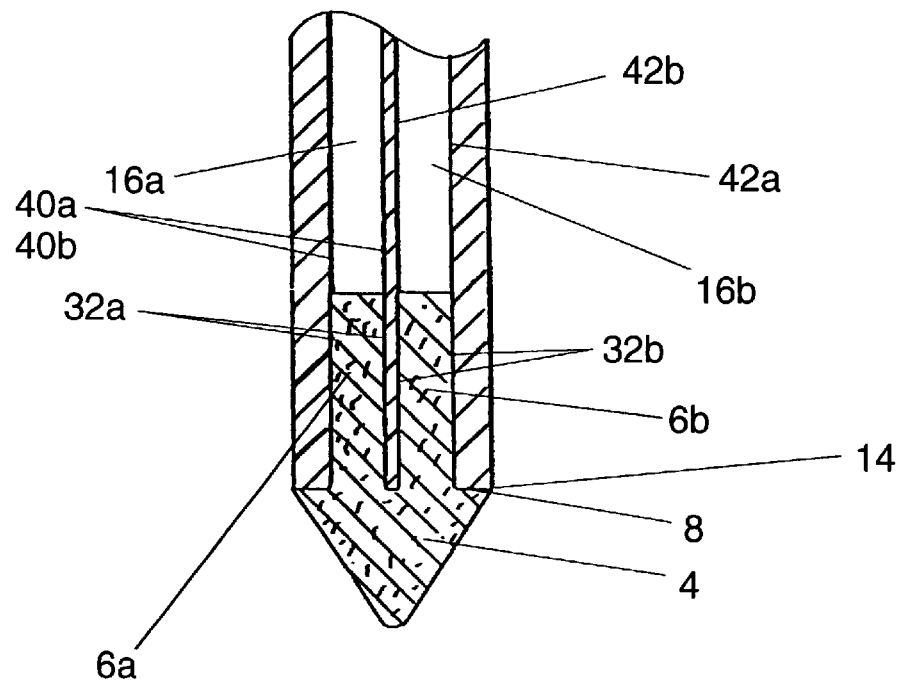
FIG. 8 is a cross-sectional side view of a second embodiment for the ostomy tube placement tip of the present invention comprising the plug design for multiple lumen tubes.

Referring now to FIGS. 7 and 8, two embodiments of the ostomy placement tip of the present invention are shown which can be used in conjunction with multiple (in this case dual) lumen tubes. Such tubes are useful when more than one nutritional supplement or medicinal formula must be administered to the patient at or about the same time and cannot be mixed or those situations where medications/nutritional formula are being administered which can not come in contact with one another. These are variations on the cylindrical body or plug design of FIG. 1 and the skirt/body plug combination as shown in FIG. 6.

As can be seen from FIG. 6, the body portion (6) of FIG. 1 is essentially divided into two individual cylindrical body portions or stems (6a) (6b) which are inserted into and fit within their respective tubes. Whereas a dual lumen tube is shown here, the placement tip could readily be designed and manufactured to fit multiple tubes as required.

As in FIG. 6, the body portions (6a, 6b) are designed to fit within the lumens of the tubes (16a, 16b) while the outer cylindrical skirt (28) fits over and surrounds the periphery of a single tube, multi-lumen ostomy tube (as shown) or may also fit over the periphery of a cluster of a number of ostomy tubes. In either event, the placement tip is designed specifically for a particular design or configuration of tubes such that there is a snug, but not tight fit between the lumens (16a, 16b) and cylindrical bodies (6a, 6b) as well as the outer periphery of the tubes (30) and the inner wall (30) of the skirt (28). Again, this allows for detachment of the tip using pressurized air, water or a stylet once the tube is properly placed.

The ostomy tube placement tip of FIG. 8 is essentially the same design of FIG. 1 as noted above but modified to fit a multi-lumen tube or more than one tube at the same time. The tip is comprised of a pyramidal-shaped head portion (4) and a substantially cylindrically-shaped body portion that is divided into stems or rods (6a, 6b) to fit into the lumens of the associated ostomy tubes (16a, 16b). When properly inserted, the base (8) of the cap or head portion (4) is flushed with the tip of the tube (14). The outer periphery of the cap (38) is substantially aligned with the circumference of the tube (12). This is preferably the relationship yet it is also conceivable that the head diameter could be a little larger than the circumference of the tip. However, a close alignment insures the least amount of friction against the sensitive body tissues when the tube is being inserted. Again, the cylindrical body portions (6a, 6b) closely match the diameters of the lumens to result in a snug but not tight fit created by the frictional resistance between the outer wall of the body portions (32a, 32b) and the inner wall of the ostomy tube lumens (40a, 40b) (42a, 42b).

What is claimed is:

1. A method for the insertion of a gastrostomy or jejunal feeding tube into an ostomy of a patient comprising the attachment of a placement tip comprising a substantially tapered head portion comprising a planar base and a substantially cylindrical body portion substantially perpendicular to the base to the end of a gastrostomy or jejunal feeding tube by inserting the body portion of said tip into the end of said tube to plug said tube, placing the tip against the ostomy of said patient and applying pressure on the tube against the patients body until the attached tip dilates the ostomy so as to allow for the entry of the tube into the ostomy, and thereafter exerting fluid pressure into the tube and detaching the tip inside the patient.

2. The method of claim 1 wherein said tip and associated feeding tube are pressed downward into the lumen of the stomach or small intestine.

3. The method of claim 2 wherein said tip is detached from the lumen of the gastrostomy tube after insertion so that both the conical head and cylindrical base portions are expelled into the patient's gastro-intestinal system for digestion and/or excretion.

4. A detachable placement tip for the insertion of a catheter or ostomy tube into a patient;
- said tip comprised of a soluble or digestible material selected from the group consisting of cellulose and its derivatives, starch and its derivatives, amylose, amylopectin, pectin, guar gum, xanthan gum, acacia gum, and mixtures thereof;
- said tip comprising a substantially tapered head portion comprising a planar base and a body portion substantially perpendicular to the base for engaging the inner walls and plugging the end of the catheter or ostomy tube to which the tip is detachably attached;
- wherein said tapered head is configured to dilate the opening of the ostomy when said tube is placed therein; and further comprises a cylindrical skirt about the periphery of the base of said head portion;
- wherein said body portion is comprised of more than one substantially cylindrical stems that are insertable within the hollow lumen of a multi-lumen catheter or ostomy tube prior to placing said tube within a surgically incised ostomy;
- wherein a circular well is formed between said skirt and said body portion for receiving said catheter or ostomy tube when said body is inserted within the lumen of said catheter or ostomy tube;
- said body portion being readily removable by fluid pressure from within the lumen of the tube.

5. The placement tip of claim 4 wherein said cylindrical stems may be inserted into the lumens of more than one catheter or ostomy tube.

* * * * *